United States Patent
Lee et al.

(10) Patent No.: US 6,770,470 B2
(45) Date of Patent: Aug. 3, 2004

(54) STRAIN FOR DECOMPOSING TMAH, AND METHOD OF WASTEWATER TREATMENT USING THE SAME

(75) Inventors: Daesang Lee, Taejon (KR);
Mi-Kyoung Lee, Tongyeong (KR);
Key-Jung Kang, Taejon (KR);
Chul-Soo Shin, Taejon (KR);
Jeong-Hwan Yun, Taejon (KR);
Do-Young Yum, Taejon (KR); Jung-Ki Lee, Taejon (KR); Kee-Don Park, Taejon (KR); Ho-Joon Choi, Taejon (KR); Bon-Tag Koo, Taejon (KR)

(73) Assignee: Inbionet Corporation, Taejon (KR)

( * ) Notice: Subject to any disclaimer, the term of this patent is extended or adjusted under 35 U.S.C. 154(b) by 0 days.

(21) Appl. No.: 10/070,316

(22) PCT Filed: Apr. 7, 2001

(86) PCT No.: PCT/KR01/00583

§ 371 (c)(1),
(2), (4) Date: Mar. 5, 2002

(87) PCT Pub. No.: WO02/08385

PCT Pub. Date: Jan. 31, 2002

(65) Prior Publication Data

US 2003/0008377 A1 Jan. 9, 2003

(30) Foreign Application Priority Data

Jul. 22, 2000 (KR) .......................................... 2000-42271
Jul. 22, 2000 (KR) .......................................... 2000-42272
Jul. 22, 2000 (KR) .......................................... 2000-42273

(51) Int. Cl.$^7$ .............................. C12N 1/20; C12N 1/12; C12N 1/16; C07F 1/00
(52) U.S. Cl. .................... 435/252.1; 435/262; 435/264; 210/601; 210/603; 210/605; 210/611
(58) Field of Search .............................. 435/252.1, 435, 435/262, 264; 210/601, 603, 605, 611

(56) References Cited

U.S. PATENT DOCUMENTS

| | | | | |
|---|---|---|---|---|
| 5,423,988 A | * | 6/1995 | Yamasaki et al. | 210/611 |
| 5,532,162 A | * | 7/1996 | Aamot | 435/264 |
| 5,702,604 A | * | 12/1997 | Yamasaki et al. | 210/603 |
| 5,868,934 A | * | 2/1999 | Yamasaki et al. | 210/605 |
| 6,056,876 A | * | 5/2000 | Yamasaki et al. | 210/617 |

* cited by examiner

*Primary Examiner*—Herbert J. Lilling
(74) *Attorney, Agent, or Firm*—Staas & Halsey LLP

(57) ABSTRACT

The present invention describes a wastewater treatment method by a microorganism decomposing Tetramethyl Ammonium Hydroxide (TMAH) which, utilized in etching the surface of silicone chip in semiconductor manufacturing process, is toxic and hard to decompose. The present invention provides novel microorganisms capable of decomposing TMAH. Also, the present invention provides a treatment method for wastewater containing TMAH, using the microorganisms. The present invention is useful in industrial field as an environmental friendly wastewater treatment method by decomposing over 90% of TMAH, one of environmental contamination materials in the wastewater of semiconductor factory.

5 Claims, 15 Drawing Sheets

STRAIN FOR DECOMPOSING TMAH, AND METHOD OF WASTEWATER TREATMENT USING THE SAME

TECHNICAL FIELD

The present invention relates to novel microorganism strains decomposing tetramethyl ammonium hydroxide; TMAH) and wastewater treatment method by applying the above strains.

More particularly, the present invention relates to novel strains decomposing tetramethyl ammonium hydroxide which is utilized for etching the surface of silicon chip while manufacturing semiconductors and is toxic and hard to be degraded. In addition, the present invention relates to wastewater treatment method which comprises applying the above strains into TMAH—containing wastewater and then performing batch culture or various kinds of continuous culture for purging the wastewater.

BACKGROUND ART

Recently, internet and information technology (IT) industries have been developed and the semiconductor demand also increased explosively. However, the development of the semiconductor industry induces the use of chemical substance gradually. Precisely, tetramethyl ammonium hydroxide (TMAH) which is utilized for etching the surface of silicone chip while manufacturing semiconductors has been exhausted in increased amounts.

TMAH is very toxic (toxicity $LC_{50}$=460 ppm) and cannot be biodegraded easily. Hence, TMAH makes biological oxygen demand (BOD) fluctuate extremely in the wastewater treatment facilities of semiconductor manufacturing plant. Therefore, the removal of TMAH from industrial wastewater has become a very important issue in order to protect environment.

Presently, some treatment method has been disclosed for eliminating TMAH from wastewater. In detail, concentration method that comprises concentrating TMAH from the wastewater by using ion exchange resin column, ultra filtration (UF) or reverse osmosis (RO), and disposing TMAH, has been reported. In addition, super-critical treatment method that comprises burning the concentrated TMAH has been demonstrated. Unfortunately, such traditional treatment methods require complicated processes and provokes secondary contamination problems accompanied the said concentration or combustion.

Therefore, more economical and efficient processes for treating TMAH should be developed in order to satisfy the increasing need of environment protection.

To overcome the foregoing and other disadvantages, we, the inventors of the present invention, have developed biological treatment processes which can decompose and eliminate TMAH efficiently even in mild conditions. First, novel microorganism strains which were insensitive to TMAH and utilized TMAH as a sole carbon and energy source have been separated. In addition, we have confirmed that the above strains could reduce the biological oxygen demand (BOD) remarkably when the strains is applied to wastewater containing TMAH.

DISCLOSURE OF INVENTION

The object of the present invention is to provide novel microorganism strains that can degrade tetramethyl ammonium hydroxide (TMAH).

Further object of the present invention is to provide biological treatment methods for TMAH containing wastewater by applying the said strains.

The present invention provides novel microorganism strains capable of decomposing tetramethyl ammonium hydroxide (TMAH), which is often utilized in etching the surface of silicone chip and, is toxic and hard to be degraded. In addition, the present invention provides TMAH containing wastewater treatment methods using the above strains.

The microorganism strains of the present invention is separated and identified by the process comprising steps as follows.

Wastewater sample is obtained from the domestic factory manufacturing semiconductors and is inoculated into the nutrient culture medium for enriching the microorganism of said wastewater primarily. Then, the strains grown above are again cultivated on the Nutrient culture medium containing TMAH. 7 strains out of the above are separated according to the cell survival, namely insensibility to TMAH. In particular, 7 TMAH insensitive strains are first separated and then designated with IBN-H1~IBN-H7 respectively. Furthermore, three strains, IBN-H1, IBN-H4, IBN-H7 superior in decomposing TMAH, are selected among the above strains.

The 3 adopted strains, IBN-H1, IBN-H4, IBN-H7, are examined by BIOLOG system, MIDI, partial nucleotide sequence determination of 16s RNA and so on. As a result, the above strains are identified to be novel strains corresponding to *Kluyveromyces delphensis, Bacillus cereus* and *Acinetobacter sp.* respectively. The strains obtained above are named with *Kluyveromyces delphensis* IBN-H1, *Bacillus cereus* IBN-H4 and *Acinetobacter sp.* IBN-H7 respectively and have been deposited in the Korean Collection for Type Cultures (KCTC) of the Korean Research Institute of Bioscience and Biotechnology (KRIBB), an international deposit organization, #52, Oun-dong, Yusong-ku, Taejon 305–333, Republic of Korea on Jul. 18, 2000, and identified as KCTC accession numbers, KCTC 0834 BP, KCTC 0835 BP and KCTC 0836 BP.

It is confirmed that all the strains selected above can grow up to the OD value 0:2 in the minimal culture medium containing TMAH as a sole carbon source and essential mineral components. In addition, the strains can also grow in both 25° C. and 30° C. without variations and can grow well even in normal or weakly acidic condition.

The microorganism strains of the present invention are insensitive to TMAH and uses TMAH as a sole carbon source for cell growth. Hence, they are exploited in the biological wastewater treatment method for removing TMAH. In this process, one strain or more than one strains selected among the group comprising *Kluyveromyces delphensis, Bacillus cereus* and *Acinetobacter sp.* can be utilized in sole or mixed culture state, preferably.

The biological wastewater treatment process for removing TMAH of wastewater, which utilizes the microorganism strain of the present invention, can be performed by using the batch culture process. Preferably, the wastewater treatment process is performed by the fed-batch culture or the continuous culture for the efficiency and the continuation of the above process. In the continuous culture system, the microorganism strain is inoculated into a fermentation vessel containing the Nutrient culture medium and is cultivated by using the batch culture process until the density reaches certain point. For example, the OD value is above 0.15. Then wastewater containing TMAH become passed through at the definite dilution velocity.

In the mean time, whatever culture process is adopted, the above stains can be fixed onto a supporting carrier preferably. The carrier facilitates said processes since it enables the strains to be used repeatedly and to remove wastewater conveniently. The carrier substance can be selected preferably among alginate, urethane foam and so on, which are conventional material for the microorganism fixation.

BEST MODE FOR CARRYING OUT THE INVENTION

Practically and presently preferred embodiments of the present invention are illustrative as shown below.

However, it will be appreciated that those skilled in the art, on consideration of this disclosure, may make modifications and improvements within the scope of the present invention.

Preferred Embodiment 1: Separation of Microorganism Strains Insensitive to TMAH (1) Proliferation of Cell Strains Existed in Wastewater of Semiconductor Factory Wastewater samples, such as influent, mixed water and return sludge were obtained from the wastewater treatment process of domestic semiconductor manufacturing companies.

The samples prepared above were diluted successively and smeared onto the Nutrient agar plate including sufficient carbon sources (beef extract 0.3% (DIFCO), peptone 0.5% (DIFCO), agar 1.5% (DIFCO)). Then the plate was cultivated with incubator at 30° C. for 18 hours.

(2) Separation of TMAH Insensitive Strains

In order to separate the strains of the present invention, the insensibility to TMAH was examined in all the strains obtained from the above proliferation stage.

The Nutrient culture medium including sufficient carbon sources (beef extract 0.3% (DIFCO); peptone 0.5% (DIFCO)) was prepared, in which TMAH concentration was adjusted to 0.25%, 0.5%, 1.0% and 2.0% respectively. Then the strains proliferated above were inoculated and were cultivated with incubator at 30° C. by shaking at 250 rpm velocity.

By the process described above, the 7 strains which proliferated and were distinguished with naked eyes were selected from the culture medium. The 7 strains were named with IBN-H1~IBN-H7 respectively. Then the final culture medium solutions obtained above were suspended with the successive dilution method and were smeared onto the above Nutrient agar plate. In addition, the total cell number was represented as colony forming unit (CFU) appearing from 1 ml of culture medium (see FIG. 1).

Figure 1:
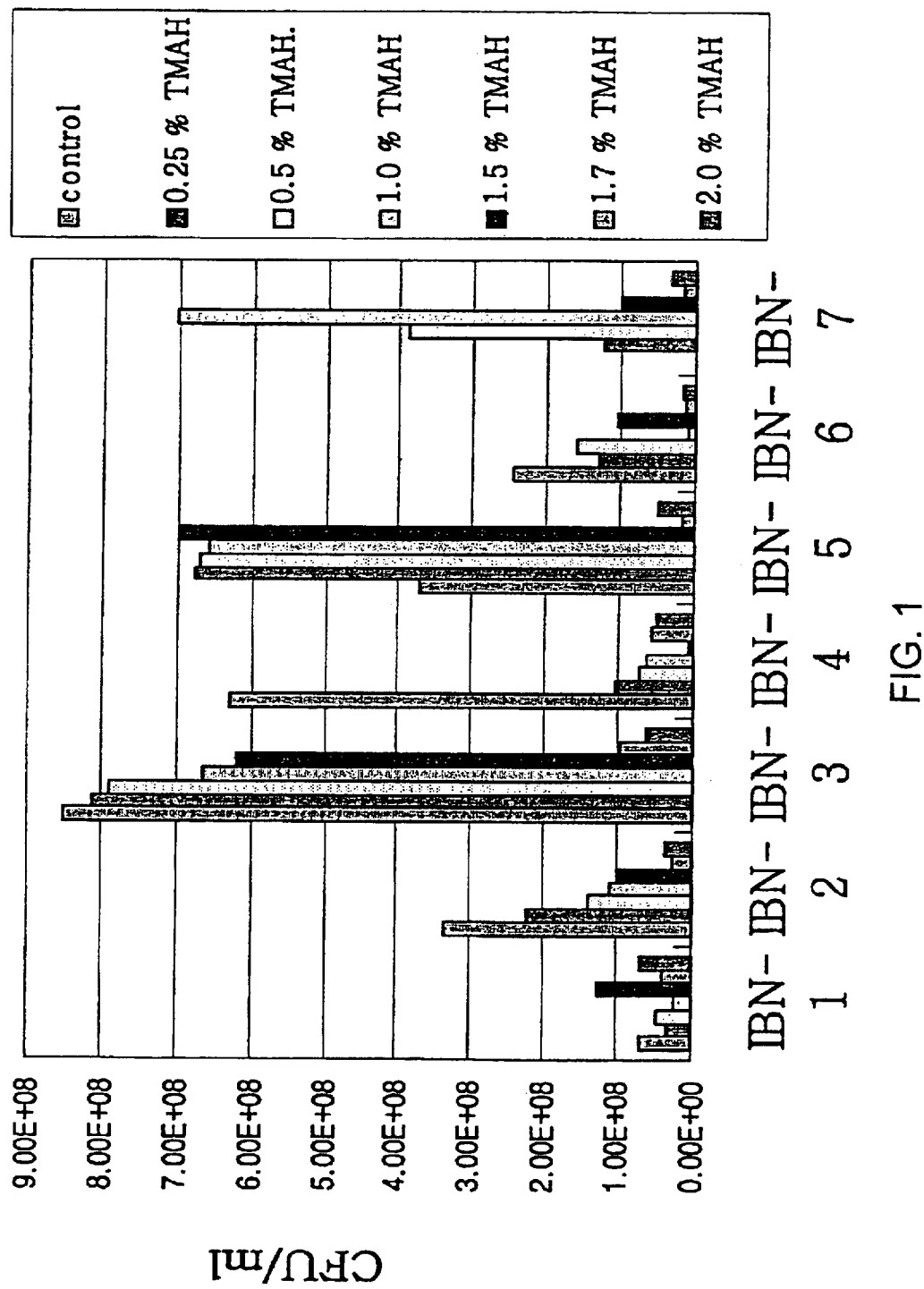
FIG. 1 shows the survival density of the strains of the present invention according to the TMAH concentration.

As depicted in FIG. 1, all the 7 strains selected from the above process have seldom grown in the medium condition containing more than 1.7% of TMAH. In particular, the IBN-H3, IBN-H4, IBN-H5 and IBN-H7 strains can proliferate actively at the concentration less than the above.

Preferred Embodiment 2: Examination of TMAH Decomposition Ratio by the TMAH Insensitive Strains Separated Above The TMAH decomposition ratio by the TMAH insensitive strains selected in Preferred Embodiment 1 was measured as follows.

The minimal culture medium including essential mineral components for cell growth (($NH_4)_2SO_4$ 3 g/L, trace element ($H_3BO_3$ 0.3 g, $CoSO_4.7H_2O$ 0.2 g, $ZnSO_4.H_2O$ 0.1 g, $MnCl_2.H_2O$ 0.03 g, $NaMoO_4.H_2O$ 0.03 g, $NiCl_2.H_2O$ 0.02 g, $CuSo_4.H_2O$ 0.01 g, $FeSO_4.H_2O$ 20 g, $CaCl_4.H_2O$ 10 g/L) 2 ml/L, $MgSO_4$ $7H_2O$ (40%) 2 ml/L, 1 M of phosphate salt buffer solution (pH 7)) was mixed with 1% TMAH as a carbon source. Then the strains of the present invention were cultivated with the above culture medium by shaking at 30° C. for 72 hours.

The BOD of the final culture medium was measured by performing triple tests. As a result, the removal ratio of TMAH was confirmed to be more than 90% in the IBN-H1, IBN-H4, IBN-HG and IBN-H7 strains (see Table 1).

TABLE 1

Removal ratio of TMAH in the strains of the present invention

| TAG | TMAH conc. before dilution | TMAH conc. after $10^{-2}$ dilution | expected BOD | sample | BOD | | | removal ratio |
|---|---|---|---|---|---|---|---|---|
| | | | | | $DO_0$ | $DO_5$ | $BOD_5$ | |
| IBN-H1 | 1% | 100 ppm | 180→150~50 | 10 | 9.1 | 8.75 | 10.5 | 94.2% |

TABLE 1-continued

Removal ratio of TMAH in the strains of the present invention

| TAG | TMAH conc. before dilution | TMAH conc. after $10^{-2}$ dilution | expected BOD | BOD sample | $DO_0$ | $DO_5$ | $BOD_5$ | removal ratio |
|---|---|---|---|---|---|---|---|---|
| IBN-H2 | 1% | 100 ppm | 180→150~50 | 10 | 9.15 | 6.55 | 78 | 56.7% |
| IBN-H3 | 1% | 100 ppm | 180→150~50 | 10 | 9.2 | 6.45 | 82.5 | 54.2% |
| IBN-H4 | 1% | 100 ppm | 180→150~50 | 10 | 9.2 | 9.05 | 4.5 | 9.75% |
| IBN-H5 | 1% | 100 ppm | 180→150~50 | 10 | 9.15 | 6.2 | 88.5 | 50.8% |
| IBN-H6 | 1% | 100 ppm | 180→150~50 | 10 | 9.15 | 8.65 | 15 | 91.7% |
| IBN-H7 | 1% | 100 ppm | 180→150~50 | 10 | 9.2 | 9.05 | 4.5 | 97.5% |

Preferred Embodiment 3: Identification of the Microorganism Strains with Excellent Activity in Decomposing TMAH According to the processes of the Preferred Embodiments 1 and 2, 3 kinds of strains, IBN-H1, IBN-H4 and IBN-H7, showing excellent activities in decomposing TMAH were adopted. Then BIOLOG experiment, fatty acid analysis, MIDI, 168 rRNA partial nucleotide sequencing and so on were performed in order to identify the above strains.

Above all, the morphological and biochemical characteristics in the above strains of the present invention were investigated. In detail, all the 3 strains of the present invention retained catalase activity. And in Gram dyeing reaction for identifying bacteria, the IBN-H4 strain was confirmed as gram positive and the IBN-H7 strain was confirmed as grim negative (See Table 2). On the other hand, the IBN-H1 strain was not applied for the Gram dyeing reaction since it was an yeast.

TABLE 2

Morphological and biochemical properties in the strains of the present invention

|  | IBN-H1 | IBN-H4 | IBN-H7 |
|---|---|---|---|
| Mobility | no | no | no |
| Gram dyeing | — | positive | negative |
| Catalase activity | positive | positive | positive |
| Others | aerobic | aerobic | aerobic |

In order to accomplish the BIOLOG analysis for identifying the IBN-H1 strain, the cell suspension of the above strain was inoculated onto 96-well microplate that carbon source of dried state was added into and was cultivated. Then the color variation and turbidity were recognized and analyzed by comparing the results with database which consisted in the results of more than 1,400 species of standard strains (aerobic strain, anaerobic strain and yeast strains). Consequently, the IBN-H1 strain was identified to belong to *Kluyveromyces delphensis* (see Table 3).

TABLE 3

Relationship of similar strains with IBN-H1 strain of the present invention

| Similar strain | SIM | DIST | AVG | MAX |
|---|---|---|---|---|
| *Kluyveromyces delphensis* | 0.623 | 5.288 | 0.569 | 1.094 |
| *Candida glabrata* | 0.026 | 6.338 | 0.500 | 1.487 |
| *Pichia pastoris* | 0.002 | 7.239 | 0.750 | 2.338 |
| *Pichia amenthionina var pachy* | 0.001 | 7.373 | 1.150 | 6.524 |
| *Candida fluctus* | 0.000 | 7.635 | 0.313 | 0.606 |
| *Candida zeylanoides* | 0.000 | 7.997 | 0.625 | 3.537 |
| *Phodotorula hylophila* | 0.000 | 8.119 | 2.399 | 9.845 |

The fatty acid contents of the IBN-H4 and IBN-H7 strains were analyzed as follows. In the IBN-H4 strain, fatty acids with carbon number 15 were the major component and in IBN-H7 strain fatty acids with carbon number 18 were the major component resultantly (See Table 4). As depicted in Table 2, in the fatty acids of the IBN-H4 strain having carbon number 15, 23.71% was iso type which had no double bond and 8.49% was anteiso type.

TABLE 4

Analysis of cellular fatty acids within the strains of the present invention

|  | IBN-H4 | IBN-H7 |
|---|---|---|
| C12:0 |  | 8.42 |
| C12:0 2OH |  | 2.12 |
| C12:0 3OH |  | 6.66 |
| C12:0 iso | 1.08 |  |
| C13:0 iso | 7.48 |  |
| C13:0 anteiso | 2.24 |  |
| C14:0 iso | 6.26 |  |
| C14:0 | 2.28 | 1.82 |
| C15:0 iso | 23.71 |  |
| C15:0 anteiso | 8.49 |  |
| C16:1 iso I/C 14:0 3OH | 3.37 |  |

TABLE 4-continued

Analysis of cellular fatty acids within the strains of the present invention

|  | IBN-H4 | IBN-H7 |
|---|---|---|
| C16:0 iso | 9.40 | |
| C16:1 wllc | | |
| C15:0 iso 2OH/C 16:1 w7c | 8.84 | 30.62 |
| C16:0 | 6.72 | 14.31 |
| C15:0 iso 3OH | | |
| Iso C17:1 w10c | 1.76 | |
| Iso C17:1 w5c | 3.87 | |
| C17:0 iso | | |
| C17:0 anteiso A | 1.61 | |
| C17:0 iso | 9.02 | |
| C17:0 anteiso | 3.03 | |
| C18:1 w9c | | 32.94 |
| C18:1 w7c | 3.03 | 1.69 |

In order to examine the sequence homology, 16s RNA partial nucleotide sequence analysis was performed by using the strains of the present invention respectively (See Sequence List; sequence number 1 and sequence number 2). Consequently, the IBN-H4 strain was shown to have 100% homology with Bacillus cereus IAM 12605T (See Table 5) and the IBN-H7 strain had 94.95% homology with *Acinetobacter calcoaceticus* ATCC 23055T (See Table 6). Therefore, the IBN-H4 and IBN-H7 strain was confirmed to belong to respective *Bacillus cereus* and Acinetobacter sp.

TABLE 5

The analysis data of 16S rRNA homology in the IBN-H4 strain of the present invention

| Strains | Homology (%) | No. of non-identical nucleotides / No. of total nucleotides |
|---|---|---|
| Bacillus cereus IAM 12605T | 100.00 | 0/584 |
| Bacillus thuringiensis IAM 12077T | 99.49 | 3/584 |
| Bacillus mycoides DSM 2048T | 99.30 | 4/571 |
| Bacillus weihenstephanensis DSM 11821T | 99.13 | 5/573 |
| Bacillus pseudomycoides DSM 12442T | 98.63 | 8/584 |
| Bacillus atrophaeus NCIB 12899T | 92.55 | 41/550 |
| Bacillus megaterium IAM 13418T | 92.45 | 44/583 |
| Bacillus cohnii DSM 6307T | 92.44 | 44/582 |
| Bacillus halmapalus DSM 8723T | 92.41 | 44/580 |
| Bacillus subtilis ATCC 6051T | 92.08 | 46/581 |
| Alicyclobacillus acidoterrestris DSM 3922T | 91.83 | 47/575 |
| Bacillus amyloliquefaciens ATCC 23350T | 91.81 | 47/574 |
| Bacillus licheniformis ATCC 14580T | 91.57 | 49/581 |
| Bacillus sporothermodurans DSM 10599T | 91.44 | 50/584 |
| Bacillus simplex DSM 1321T | 91.21 | 51/580 |
| Bacillus azotoformans ATCC 29788T | 91.12 | 49/552 |
| Bacillus psychrosaccharolyticus ATCC 23296T | 91.09 | 50/561 |
| Bacillus oleronius DSM 9356T | 91.08 | 52/583 |
| Bacillus pumilus ATCC 7061T | 90.01 | 51/567 |
| Bacillus circulans ATCC 4513T | 90.97 | 50/554 |
| Bacillus lentus IAM 12466T | 90.86 | 53/580 |
| Bacillus benzoevorans ATCC 49005T | 90.81 | 53/577 |
| Bacillus fastidiosus DSM 91T | 90.64 | 54/577 |
| Bacillus firmus IAM 12464T | 90.50 | 55/579 |
| Bacillus badius ATCC 14574T | 90.34 | 56/580 |
| Bacillus marinus DSM 1297T | 90.19 | 57/581 |

TABLE 6

The analysis data of 16S rRNA homology in the IBN H17 strain of the present invention

| Strains | Homology (%) | No. of non-identical nucleotides / No. of total nucleotides |
|---|---|---|
| Acinetobacter calcoaceticus ATCC 23055T | 94.95 | 26/515 |
| Acinetobacter haemolyticus DSM 6962T | 94.17 | 30/515 |
| Acinetobacter baumannii DSM 30007T | 93.98 | 31/515 |
| Acinetobacter lwoffii DSM 2403T | 92.82 | 37/515 |
| Acinetobacter radioresistens DSM 6976T | 92.77 | 37/512 |
| Acinetobacter johnsonii DSM 6963T | 92.23 | 40/515 |
| Acinetobacter junii DSM 6964T | 91.47 | 44/516 |

Preferred Embodiment 4: TMAH Availability in the Identified Strains of the Present Invention The IBN-H1, IBN-H4 and IBN-H7 strains of the present invention identified above were examined in order to detect whether TMAH could be utilized as a sole carbon source.

The minimal culture medium including essential, mineral components for cell growth (reference: Preferred Embodiment 2) was utilized and mixed with 0.5% TMAH as a carbon source. Then the above strains were inoculated independently and cultivated at 30° C. for 72 hours by shaking. This culture medium was diluted successively and the diluted cell suspension was smeared onto the culture plate having the same composition of the above culture medium and incubated.

The 3 strains of the present invention were observed to form colonies onto the culture plate respectively, which confirmed that the above strains could grow by using TMAH as a sole carbon source and as an energy source.

In order to investigate the difference of the strains, the availability of TMAH was examined in the strains of the present invention and other strains related with the above stains.

In detail, *Kluyveromyces dephensis* and *Saccharomyces cerevisiae* were utilized instead of the IBN-H1 strain; *Bacillus cereus, Bacillus subtilis* and *Bacillus brevis* instead of the IBN-H4 strain; and *Acinetobacter calcoaceticus* and *Acinetobacter genospecies* instead of the IBN-H7 strain respectively in order to disclose whether TMAH could be adopted as a carbon source or not.

Consequently, all the comparative strains having relationship with the strains of the present invention did not form colonies. Hence the comparative strains were confirmed not to utilize TMAH as a carbon source (See Table 7).

Therefore, the strains of the present invention were identified again to have different physiological and biochemical properties from those of conventional strains, although the strains of IBN-H1, IBN-H4 and IBN-H7 in the present invention belonged to *Kluyveromyces dephensis, Bacillus cereus* and Acinetobacter sp. respectively.

TABLE 7

Examination for the usage of TMAH as a carbon source in the selected strains of the present invention and comparative strains related with the above strains

| The stains of the present invention (comparative strains related) | Colony forming (yes/no) |
|---|---|
| *Kluyveromyces delphensis* IBN-E1 | yes |
| (*Kluyveromyces delphensis*) | no |
| (*Saccharomyces cerevisiae*) | no |
| *Bacillus cereus* IBN-H4 | yes |
| (*Bacillus cereus*) | no |
| (*Bacillus subtilis*) | no |
| (*Bacillus brevis*) | no |
| Acinetobacter sp. IBN-H7 | yes |
| (*Acintobacter calcoaceticus*) | no |
| (*Acintobacter genospecies*) | no |

Preferred Embodiment 5: TMAH Insensibility of the Identified Strains

The IBN-H1, IBN-H4 and IBN-H7 strains of the present invention identified above were examined in order to detect the TMAH insensibility.

The cell strains of the present invention and the related strains were inoculated into the Nutrient culture medium (Bacto beef extract 3 g/L, Bacto peptone 5 g/L) with 3 ml volume respectively and were cultivated at 30° C. for 18 hours by shaking. Then the culture medium of each strain was allotted to measure the absorbance (OD) at 600 nm, which would adjust the density and number of the cell strains and could facilitate the insensibility experiments. The above samples were centrifuged at 12,000 rpm for 5 minutes and were washed 3 times with saline for eliminating the remaining medium. Then the sample were resuspended by adding 1 ml of 2 TMAH and maintained at 30° C. for an hour. The cell strains were again centrifuged in order to remove the cell supernatant and washed 3 times with saline so as to remove the remaining TMAH. Then the cell samples obtained were diluted with 200 $\mu$l of physiological saline successively and were resuspended. The cell suspensions were smeared onto the agar culture plate containing Nutrient medium components and were incubated at 30° C. for 18 hours. And then the number of colonies on the above agar plate was calculated in each strain.

For controlled samples, physiological saline was utilized instead of 2% TMAH in each cell strains. In addition, the number of colonies formed in each experimental sample and comparative sample was adjusted reciprocally with that in the controlled sample, which had no TMAH for measuring exactly.

In order to compare the insensibility to TMAH, both the strains of the present invention and the strains related with the above strains were investigated for the detection.

Precisely, as a comparative strain related with the IBN-H1 strain of the present invention *Kluyveromyces dephensis* and *Saccharomyces cerevisiae* were applied; *Bacillus cereus*, *Bacillus subtilis* and *Bacillus brevis* as a strain related with the IBN-H4 strain; and *Acinetobacter calcoaceticus* and *Acinetobacter genospecies* as a strain related with the IBN-H7 strain respectively.

Consequently, all the comparative strains having relationship with the strains of the present invention formed even smaller number of colonies than the strains of the present invention. Hence the comparative strains were confirmed to be much less insensitive to TMAH (See Table 8).

Therefore, the strains of the present invention, IBN-H1, IBN-H4 and IBN-H7, were also identified to be new strains having different physiochemical properties from those of conventional strains although the above strains belonged to *Kluyveromyces dephensis*, *Bacillus cereus* and *Acinetobacter sp.* respectively.

As demonstrated above, the above strains of the present invention, IBN-H1, IBN-H4 and IBN-H7, are confirmed as new strains which have not been reported. The strains obtained above are named with *Kluyveromyces delphensis* IBN-H1, *Bacillus cereus* IBN-H4 and Acinetobacter sp. IBN-H7 respectively and have been deposited with the Korean Collection for Type Cultures (KCTC) of the Korean Research Institute of Bioscience and Biotechnology (KRIBB), an international deposit organization, #52, Oun-dong, Yusong-ku, Taejon 305–333, Republic of Korea on Jul. 18, 2000, and identified as KCTC accession numbers, KCTC 0834 BP, KCTC 0835 BP and KCTC 0836 BP.

TABLE 8

Comparison of the insensibility to TMAH in the selected strains of the present invention and the related strains

| The stains of the present invention (comparative strains related) | Insensibility to TMAH |
|---|---|
| *Kluyveromyces delphensis* IBN-H1 | 100% |
| (*Kluyveromyces delphensis*) | <10 ± 5% |
| (*Saccharomyces cerevisiae*) | <10 ± 5% |
| *Bacillus cereus* IBN-H4 | 100% |
| (*Bacillus cereus*) | <10 ± 5% |
| (*Bacillus subtilis*) | <10 ± 5% |
| (*Bacillus brevis*) | <10 ± 5% |
| Acinetobacter sp. IBN-H7 | 100% |
| (*Acintobacter calcoaceticus*) | <10 ± 5% |
| (*Acintobacter genospecies*) | <10 ± 5% |

Preferred Embodiment 6: Characteristics in Cell Growth of the Identified Strains
(1) Characteristics of Cell Growth According to Incubation Temperature In order to detect the optimal temperature for cultivating the separated strains of the present invention, the above strains were suspended by using the same culture medium with that used in Preferred Embodiment 2 and 200 $\mu$l of the culture medium was added into 96-well microplate. Then the cell in the microplate was cultured at 25° C. and 30° C. for 72 hours by shaking at 250 rpm. The OD values of the cell strains were calculated at 600 nm by using microplate reader (MR 5000, Dynatech, U.S.A.) (see FIG. 2a, FIG. 2b and FIG. 2c).

Figure 2A:
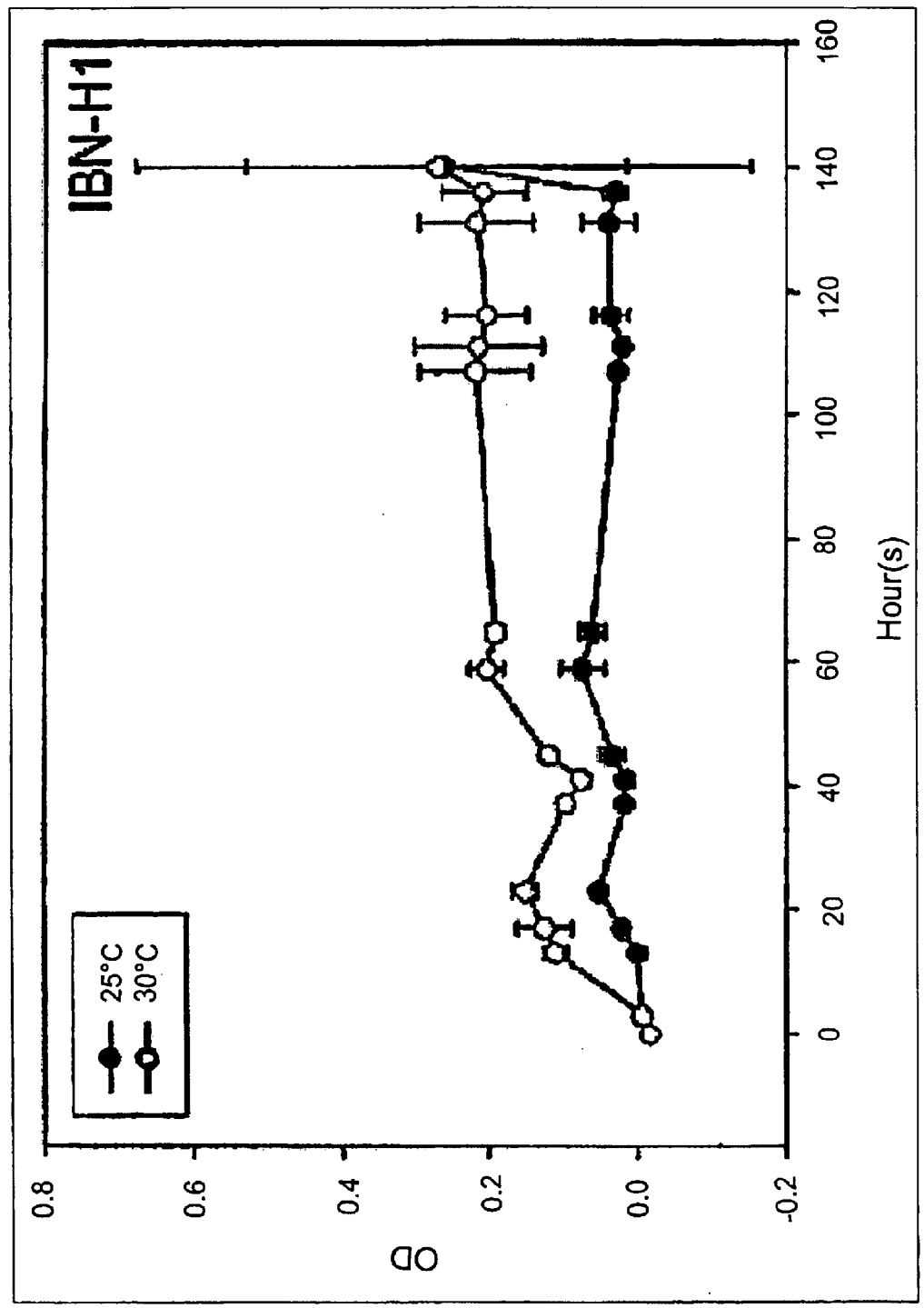
FIG. 2a shows the growth curves of IBN-H1 strain according to cell incubation temperature.
Figure 2B:
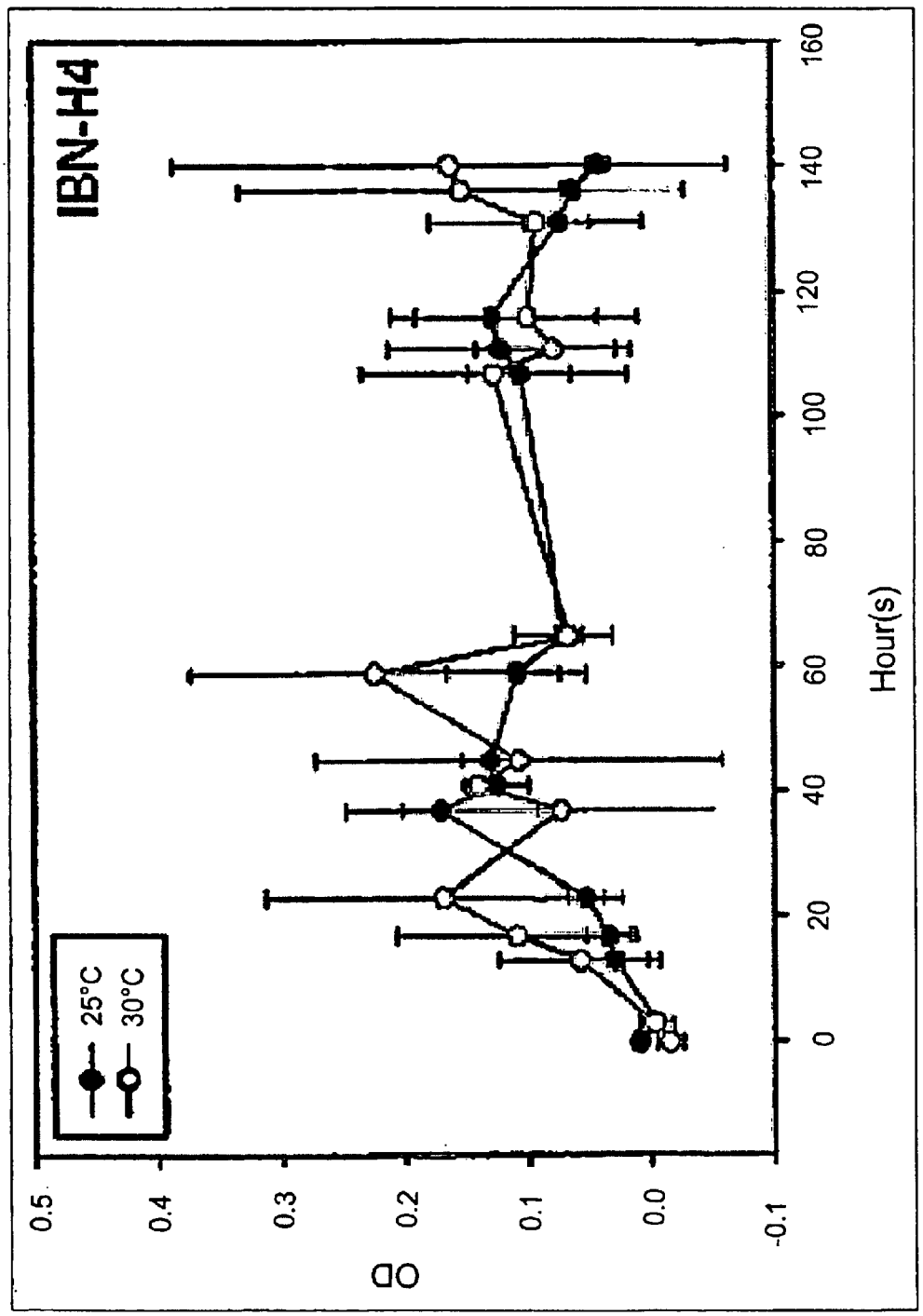
FIG. 2b shows the growth curves of IBN-H4 strain according to incubation temperature.
Figure 2C:
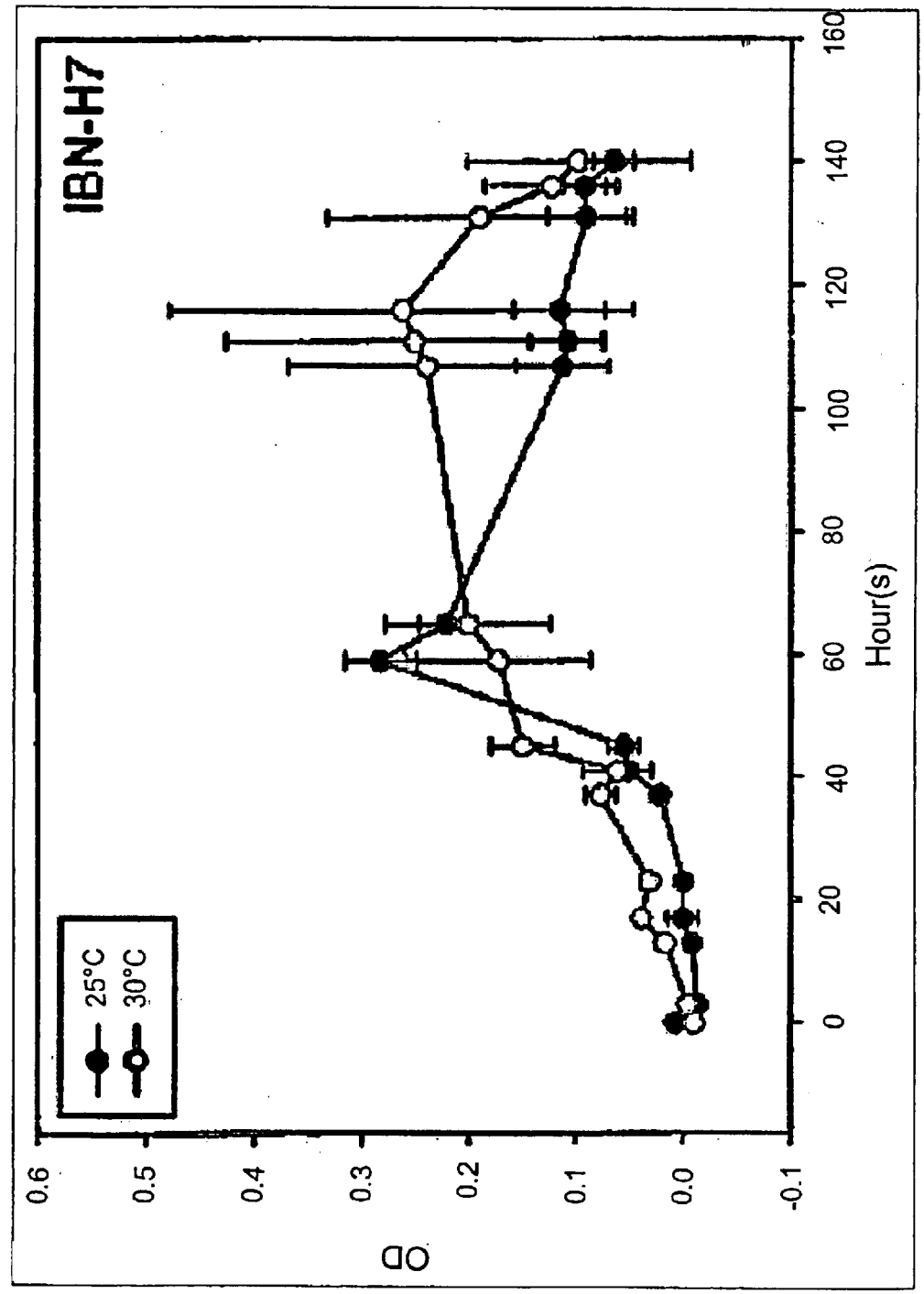
FIG. 2c shows the growth curves of IBN-H7 strain according to incubation temperature.

As described in FIG. 2a, FIG. 2b and FIG. 2c, the cell strains proliferated more actively at 30° C. than at 25° C. during the whole culturing process. In addition, the cell numbers (OD value) were maintained almost constant through culturing period at each temperature, particularly about 0.2, 0.05 in the IBN-H1 strain, about 0.15, 0.15 in the IBN-H4 strain and about 0.25, 0.15 in the IBN-H7 strain.
(2) Characteristics of Cell Growth According to pH In order to examine the optimal pH for culturing the separated strains of the present invention, the above strains was suspended by using the same culture medium with that used in Preferred Embodiment 3 and 200 $\mu$l of the culture medium was added into 96-well microplate. Then the cell in the microplate was cultured at pH 5, pH 7 and pH 9, at 30° C. for 72 hours by shaking at 250 rpm. The OD values of the strains were calculated at 600 nm by using microplate reader (MR 5000, Dynatech, USA) (see FIG. 3a, FIG. 3b and FIG. 3c).

Figure 3A:
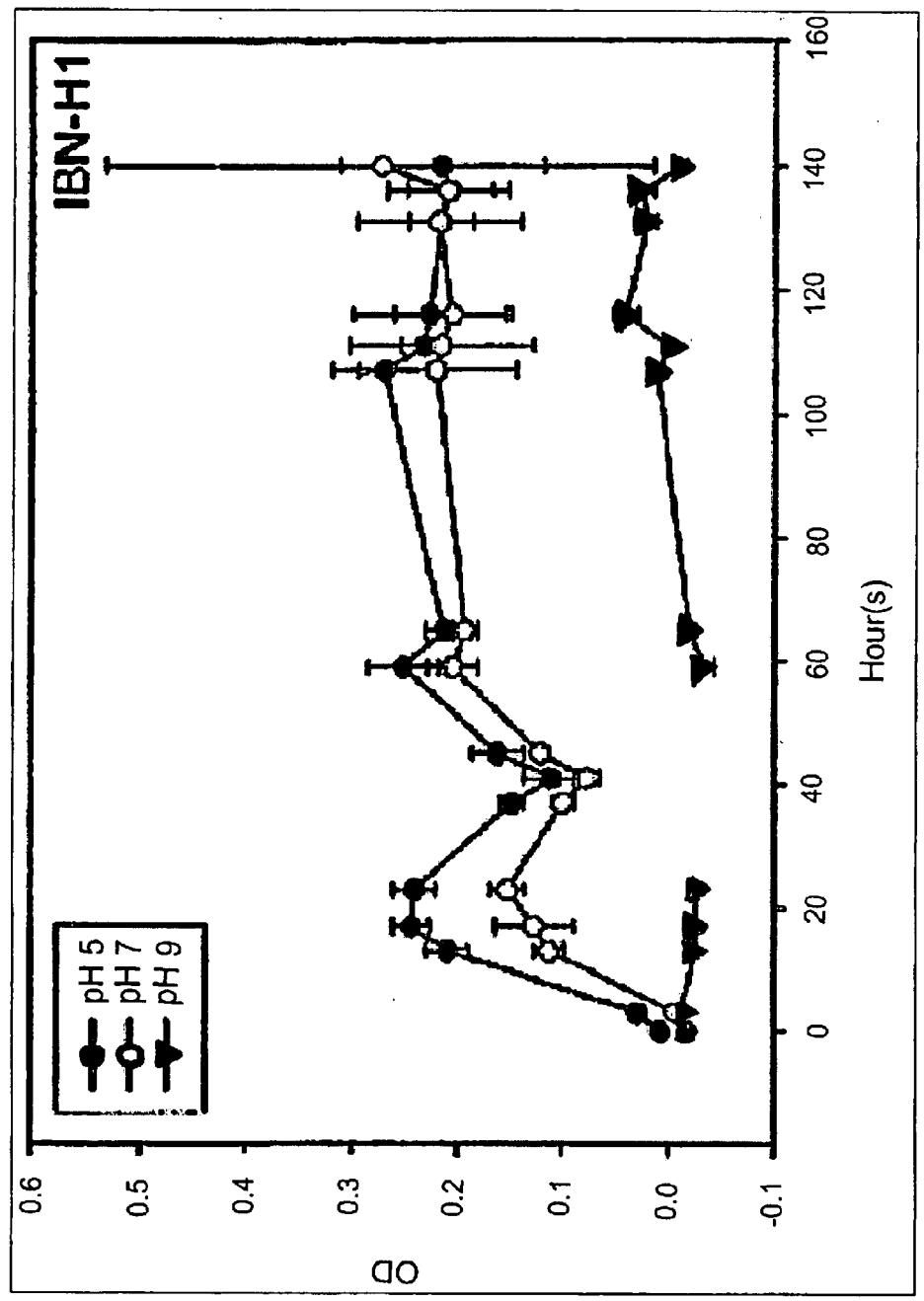
FIG. 3a shows the growth curves of IBN-H1 strain according to culture pH.
Figure 3B:
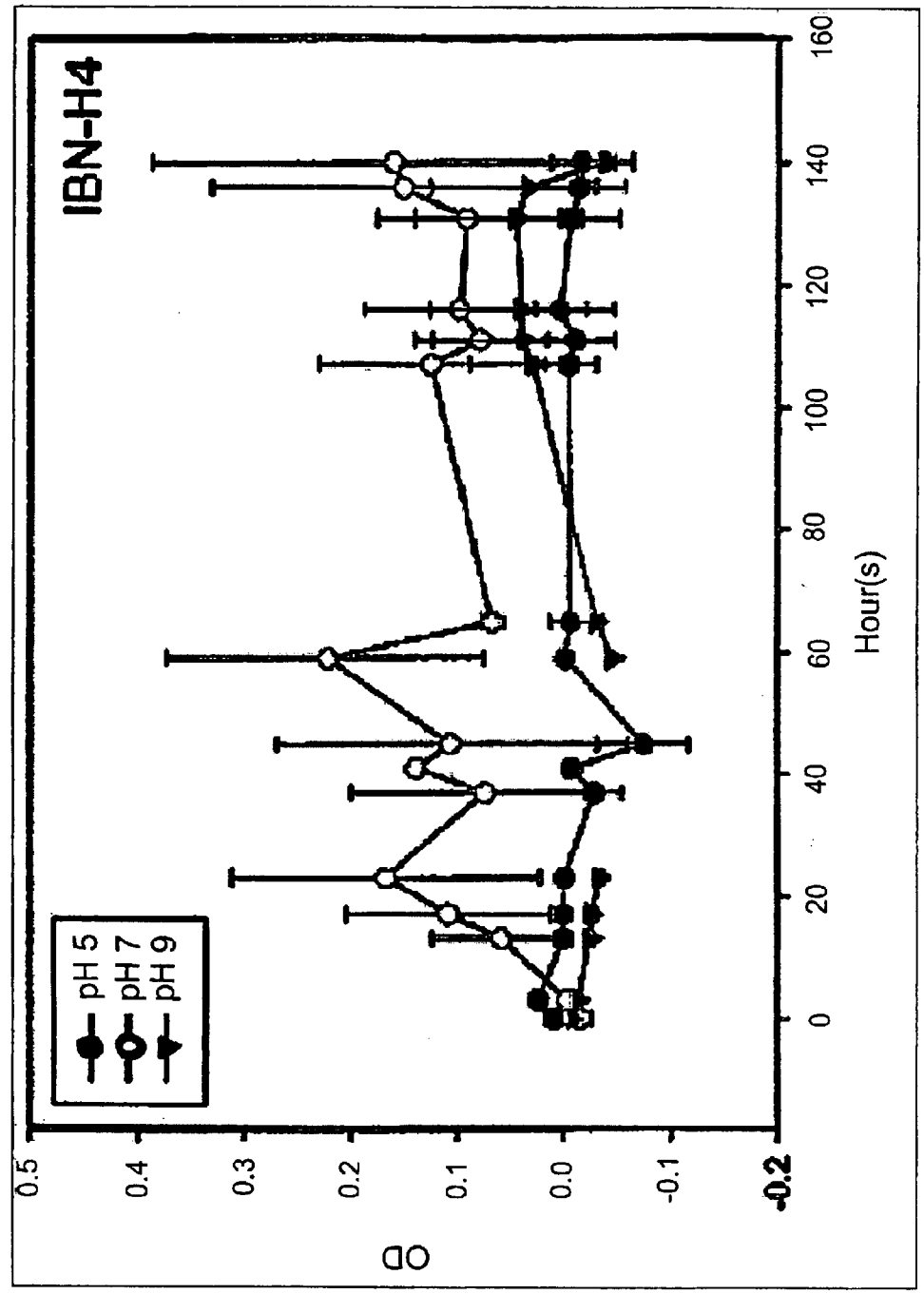
FIG. 3b shows the growth curves of IBN-H4 strain according to culture pH.
Figure 3C:
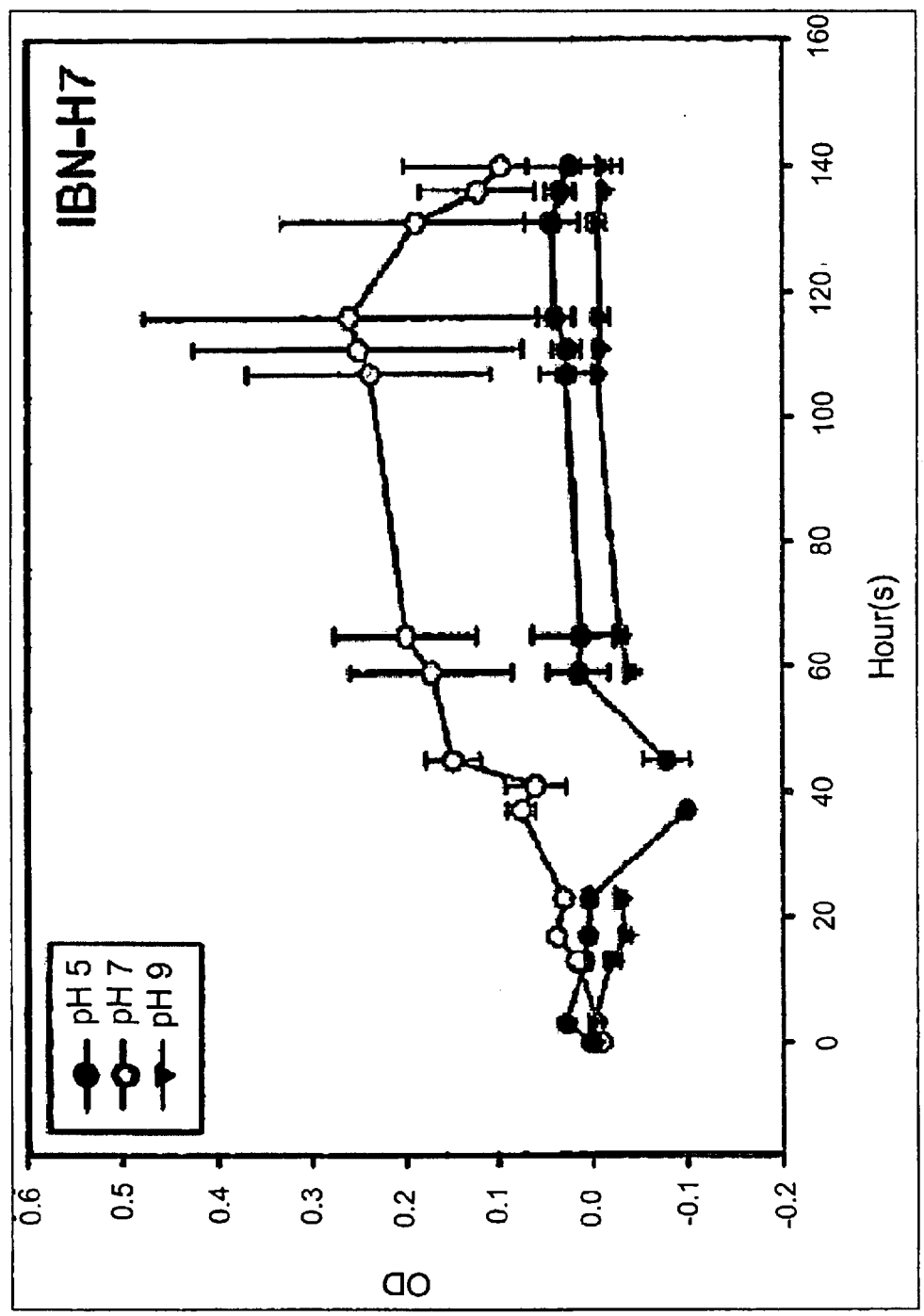
FIG. 3c shows the growth curves of IBN-H7 strain according to culture pH.

As described in FIG. 3a, FIG. 3b and FIG. 3c, in the IBN-H1 strain, the OD value in PH 5 to PH 7 range was about 0.2; in the IBN-H4 strain, the OD value at pH 7 ranges was about 0.15; and in the IBN-H7 strain, OD value at pH 7 range was 0.2 approximately. Hence, the above 3 strains were known to grow well in both the normal and weakly acidic condition.

(3) Characteristics of Cell Growth in Batch Culture By Using Culture Nedium Containing 1% TMAH In order to examine the growth pattern of the above strains while performing batch culture by using TMAH-containing culture medium, the above strains IBN-H1, IBN-H4 and IBN-H7 were cultivated with the same culture medium of Preferred Embodiment 2 at 30° C. for 72 hours by shaking at 250 rpm. The OD values of the above strains were calculated at 600 nm in every hour interval by using microplate reader (MR 5000, Dynatech, USA) and then the growth curves of the each cell strain were drawn (see FIG. 4).

Figure 4:
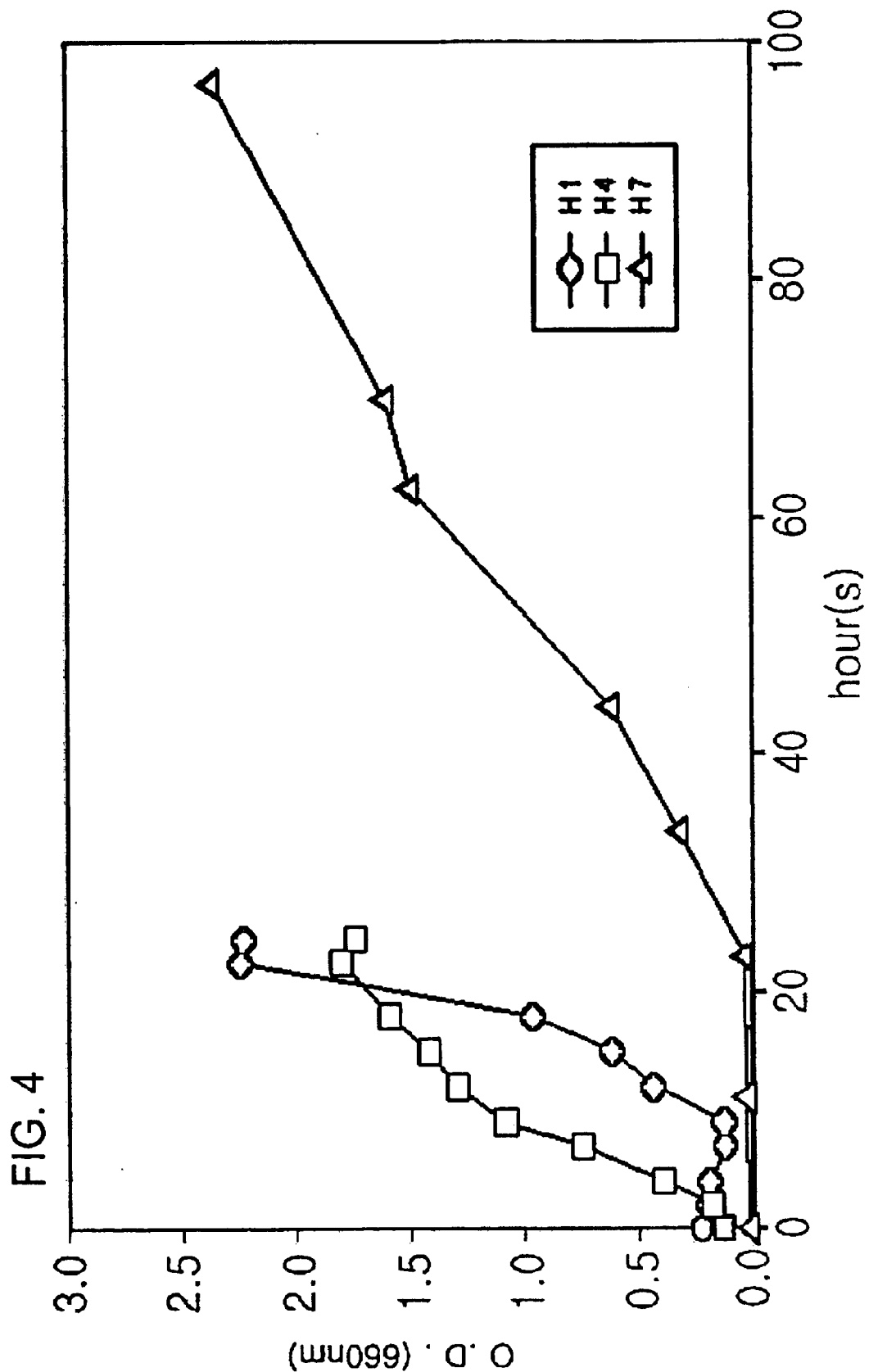
FIG. 4 shows the batch-cultured growth curves of the strains of the present invention.

Consequently as described in FIG. 4, the IBN-H1 and the IBN-H4 strains reached the maximum value of the cell growth (OD value: 2.24 and 1.80) after about 22-hour culture and the IBN-H7 strains increased the growth rate slowly until 100 hours and reached the maximum value (OD value: 2.36).

Preferred Embodiment 7: Biological TMAH Treatment Process by Using the Strains of the Present Invention The possibility of the above strains for biological treatment was investigated indirectly by applying the water treatment model for the TMAH containing wastewater and then by monitoring the cell number of the strains in culture medium.

The volume of the fermentator was 5 L, if not mentioned especially, and the initial amount of the culture medium was 3 L and the incubation temperature was 30° C.

(1) Enrichment of the Strains for Applying to the Treatment Process

In order to make practical application for the TMAH—containing wastewater treatment, the cell strains obtained in the present invention were cultivated with high density respectively.

The above strains were inoculated into the fermentation vessel with 5 L volume including 3L of Nutrient culture medium with glucose (glucose 10 g/L, yeast extract 10 g/L, $MgSO_4.7H_2O$ 1.2 g/L, $KH_2PO_4$ 13.3 g/L, $(NH_4)_2.HPO_4$ 4 gL, pH 7.0 (HCl)) independently and were cultivated at 30° C. In every 24-hour interval, high Nutrient culture medium (glucose 274 g/L, yeast extract 211 g/L, $MgSO_4.7H_2O$ 1 gL, $(NH_4)_2.HPO_4$ 1.5 g/L, pH 7.0 (HCl)) was added again by 100 ml volume. According to the process, the fed-batch culture was accomplished.

Consequently, all the 3 strains of the present invention sustained the high density which was more than 40 in the OD value. Hence, it was confirmed that the above strains could multiply so as to be applied for industrial uses.

(2) Batch Culture Treatment

The above strains, IBN-H1, IBN-H4 and IBN-H7 were inoculated into the fermentation vessel with 5 L volume including 3L of Nutrient culture medium (yeast extract 1 g/L, $MgSO_4.7H_2O$ 0.8 g/L, $KH_2PO_4$ 1 g/L, $(NH_4)_2.HPO_4$ 1 g/L, pH 7.0 (HCl)) with 1.0% TMAH independently and were cultivated at 30° C. for 70 hours in batch pattern. As a result, the OD value at 660 nm reached 2.2, 1.8 and 2.5 respectively.

Consequently, all the 3 strains of the present invention sustained the TMAH insensibility even in large scale and can utilize TMAH as a sole carbon source for cell growth. Hence, it was confirmed that the above strains could be exploited to treat wastewater containing TMAH in the batch culture pattern.

(3) Continuous Culture Treatment

The above strains, IBN-H1, IBN-H4 and IBN-H7 were cultivated respectively by using the same treatment process of the above batch culture. Then at the point that the OD value reached to 2.2, 1.8 and 2.5 respectively, the TMAH-containing culture medium and water were passed through with 0.15 of dilution ratio per hour for treating continuously.

Figure 5:
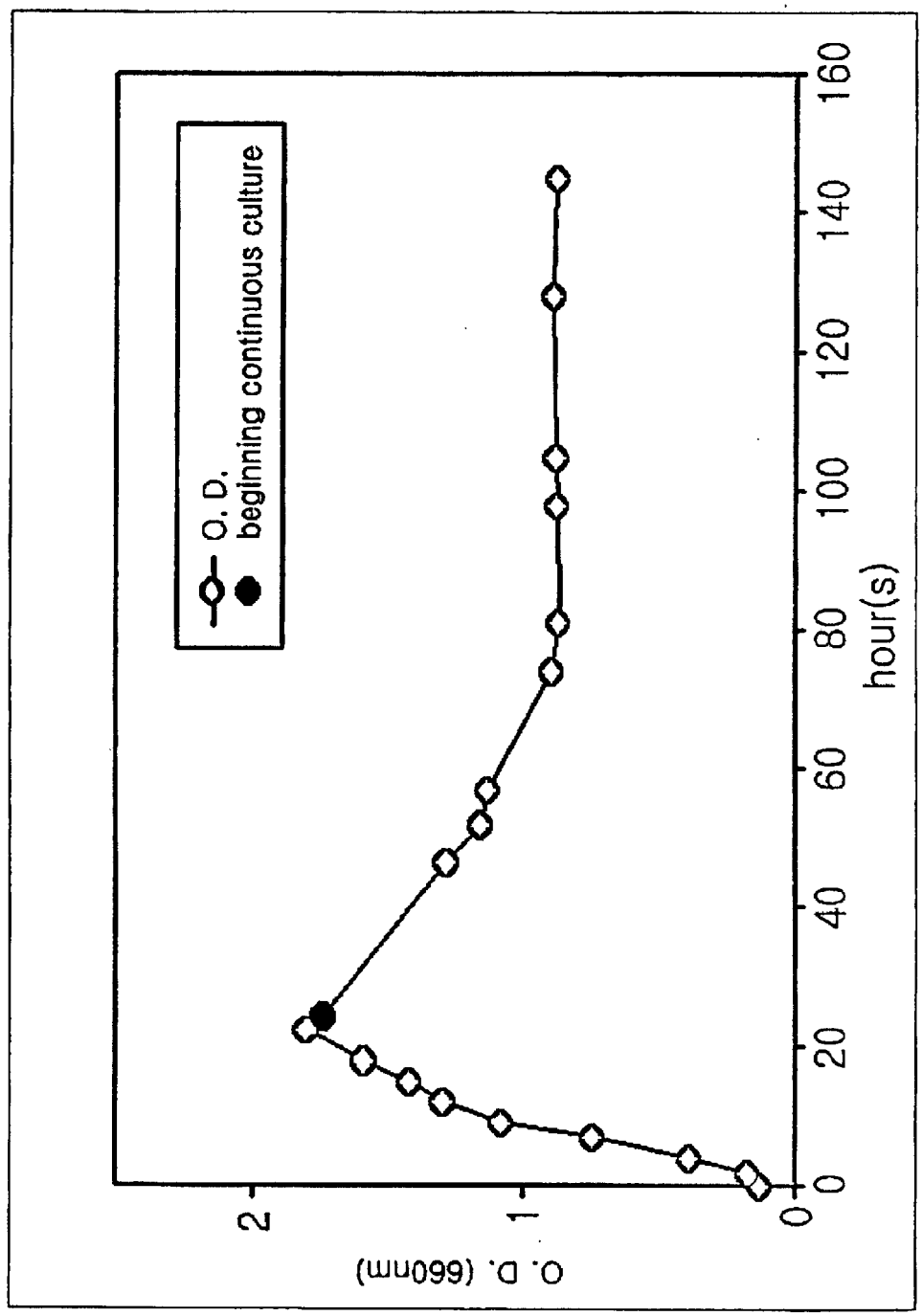
FIG. 5 shows the continuous-cultured growth curves of the IBN-H1 strain of the present invention.

Consequently, the OD values have decreased from the start point of the continuous culture and were maintained stably after about 60 hours in near 1.1, 0.9 and 1.2 of the OD value respectively (See FIG. 5).

Therefore, it was confirmed that all the 3 strains of the present invention sustained considerable cell densities even in the continuous treatment process and could be exploited to treat TMAH-containing wastewater in the continuous pattern.

In Preferred Embodiments described below, the above 3 strains of the present invention were cultivated with high densities and were mixed in the same ratio's and then were applied for performing the experiments.

(4) Recycling Continuous Culture Treatment

Figure 6:
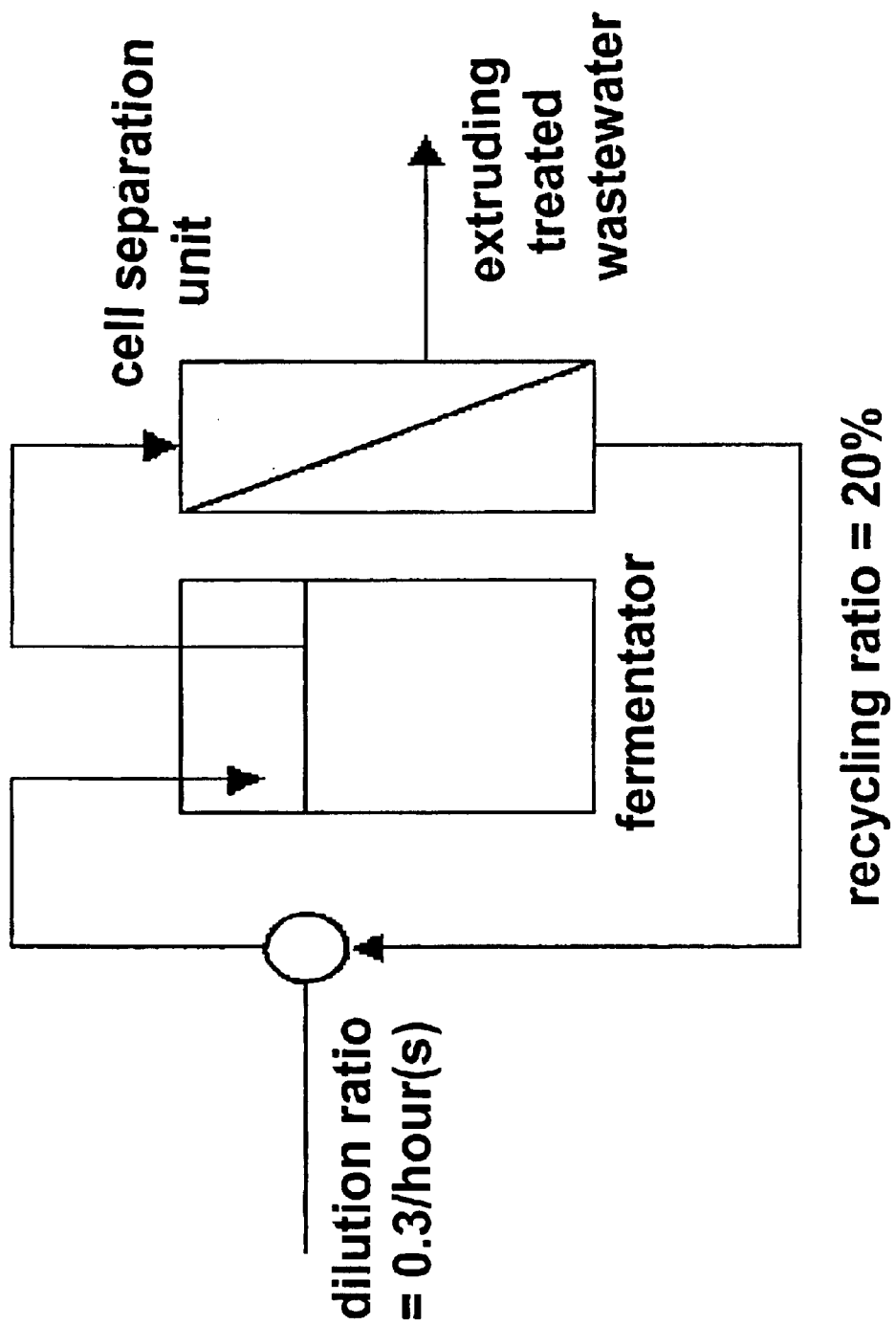
FIG. 6 shows the diagram of the recycling equipment for continuous wastewater treatment of the present invention.

As shown in FIG. 6, the recycling type continuous culture was performed by the process as follows. Precisely, the culture medium outflowing from the continuous treatment process was passed through cell separation unit which was composed of fibrous strand; and then recovered into the fermentation vessel.

At the initial stage, simple batch culture was performed. But if the OD value reached 2.0, the culture pattern was changed to the recycling continuous culture. The dilution ratio was 0.3 per hour and the plain medium corresponding to 80% volume of the culture medium was extruding from the fermentator finally. Namely, the reflection rate was adjusted to 0.2.

Figure 7:
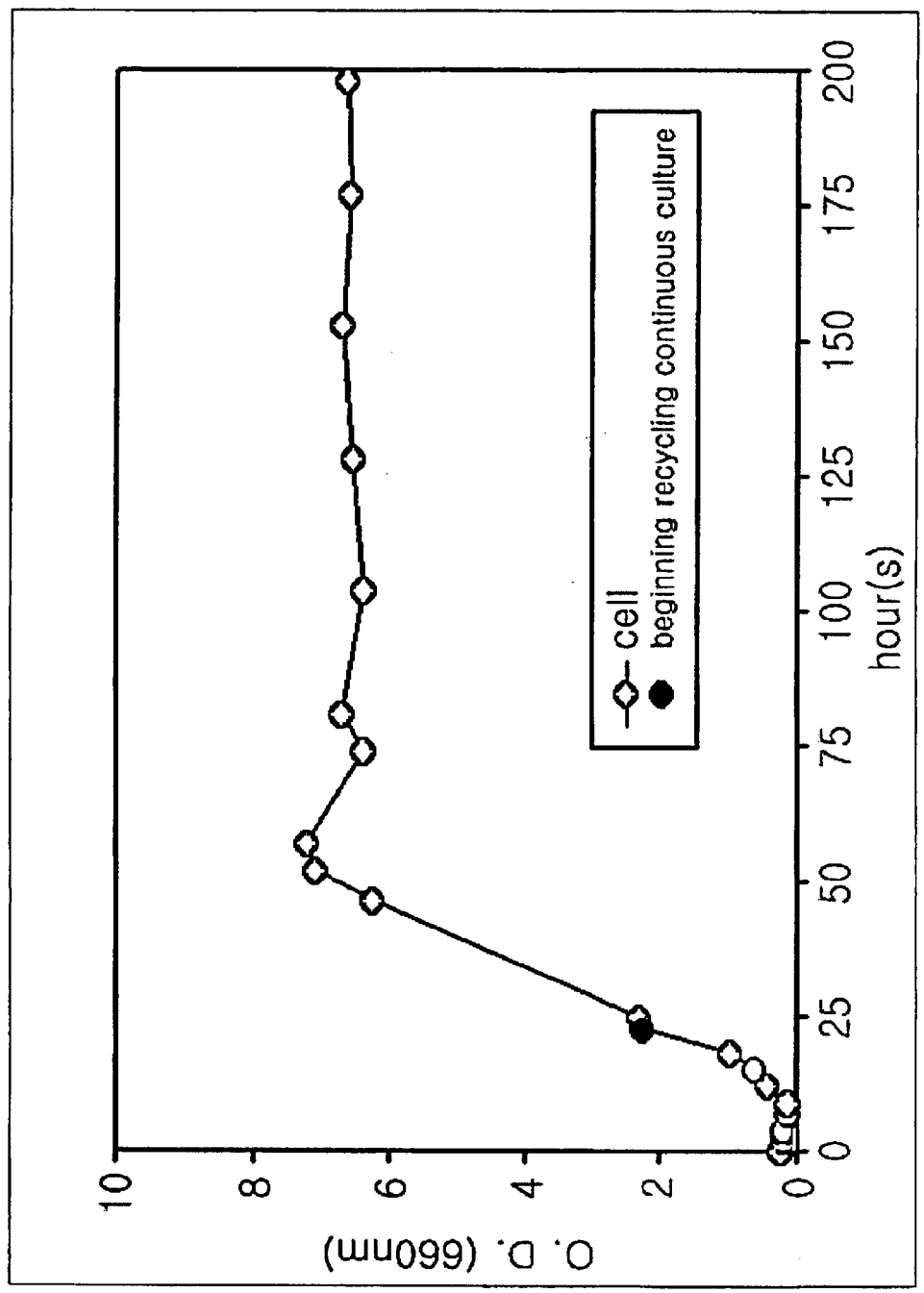
FIG. 7 shows the growth curves of the strains according to wastewater treatment by using the recycling equipment disclosed in FIG. 6.

Consequently, the OD value of the culture medium was maintained in 6~7 range stably and long when about 50 hours has passed from the initiation point (See FIG. 7).

Therefore, it was confirmed that the TMAH-containing wastewater could also be treated efficiently even by using the cell strains of the present invention and the recycling continuous culture process.

(5) Continuous Culture Treatment by Using Fluidized—Bed Reactor

According to the above process of continuous culture treatment, the cell strains were cultivated. If the OD value reached 0.2, conventional polyurethane foam (standard size; $0.5 \times 0.5 \times 0.5$ cm$^3$) which has been used in fermentator was added with 90% of the void volume for the absorption of the above strains. The resulting support with the cell strains was incubated in the continuous culture pattern.

Consequently, the same cell density can be sustained with that obtained from the simple continuous culture process although the dilution ratio (0.3 per hour) was even higher than that of the above simple continuous culture (0.5 per hour).

(6) Continuous Culture Treatment by Using Packed Bed Reactor

Figure 8:
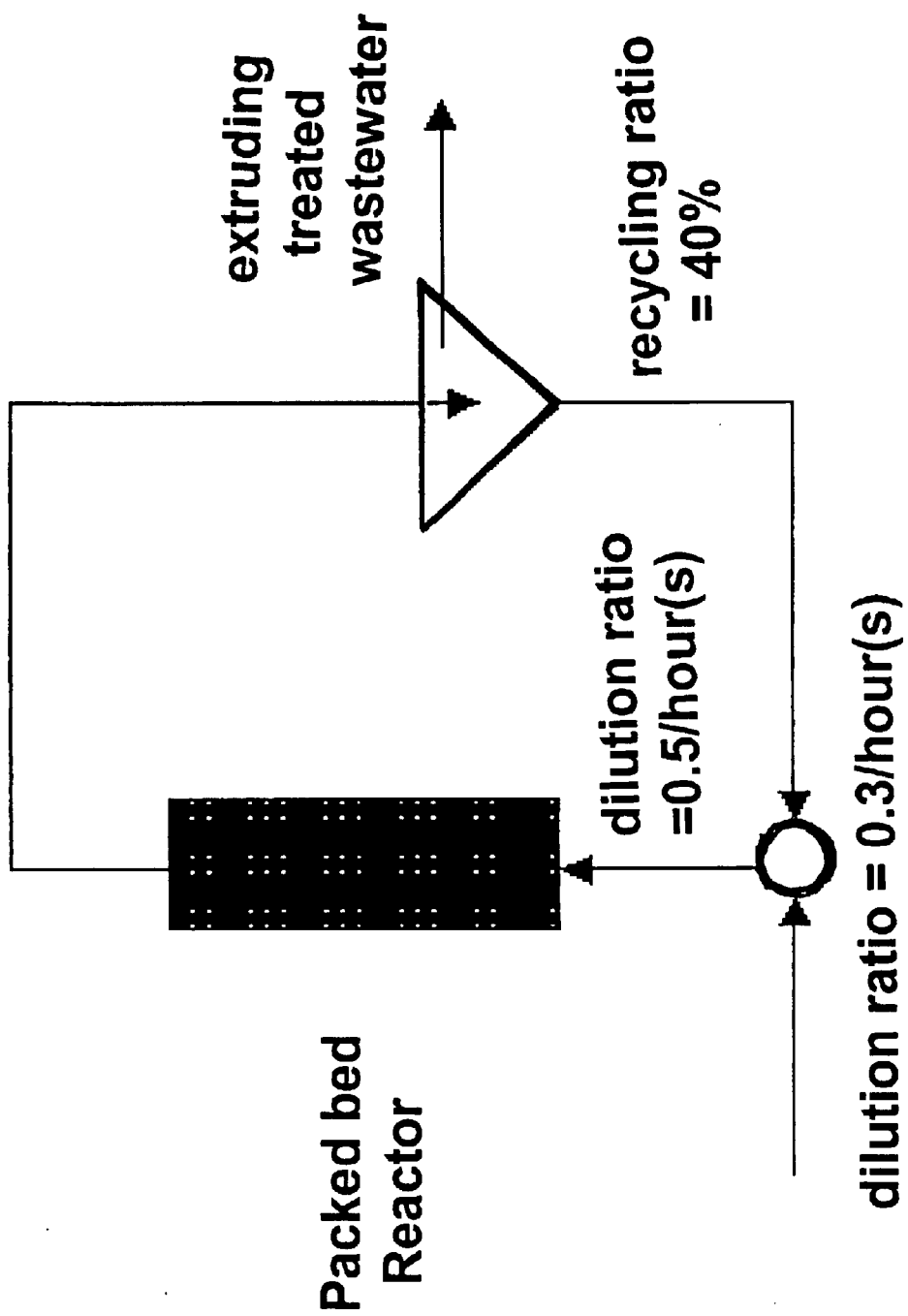
FIG. 8 shows the diagram of the wastewater treatment equipment that exploits the packed bed reactor of the present invention.

The packed bed reactor (reactor standard=radius 10, height 30 cm; void volume=70%) which was fulfilled with the polyurethane foam supporting the cell strains of the present invention was exploited. The culture medium and recycling. water were passed upward in the dilution ratio 0.3/hour and 0.2/hour respectively through the above packed bed reactor and pressure (namely, dilution ratio 0.5/hour while using the reactor as a standard). 40% (volume ratio) of extruding water from the reactor was recovered and reused with recycling water (See FIG. 8).

Consequently, the OD value was maintained at 1.4 stably during 2 months and the biological oxygen demand (BOD) has reduced from 466.5 to 169.7, which corresponded to 74% reduction.

Preferred Embodiment 8: Pilot System Experiment of Biological TMAH Treatment Process by Using the Strains of the Present Invention In order to treat wastewater containing TMAH, the pilot system was established in the semiconductor manufacturing factory (Hyundai Electronics Industries Co., Ltd; Chungju). The mixed strains composed of the novel strains of the present invention were applied for performing the biological wastewater treatment.

Figure 9A:
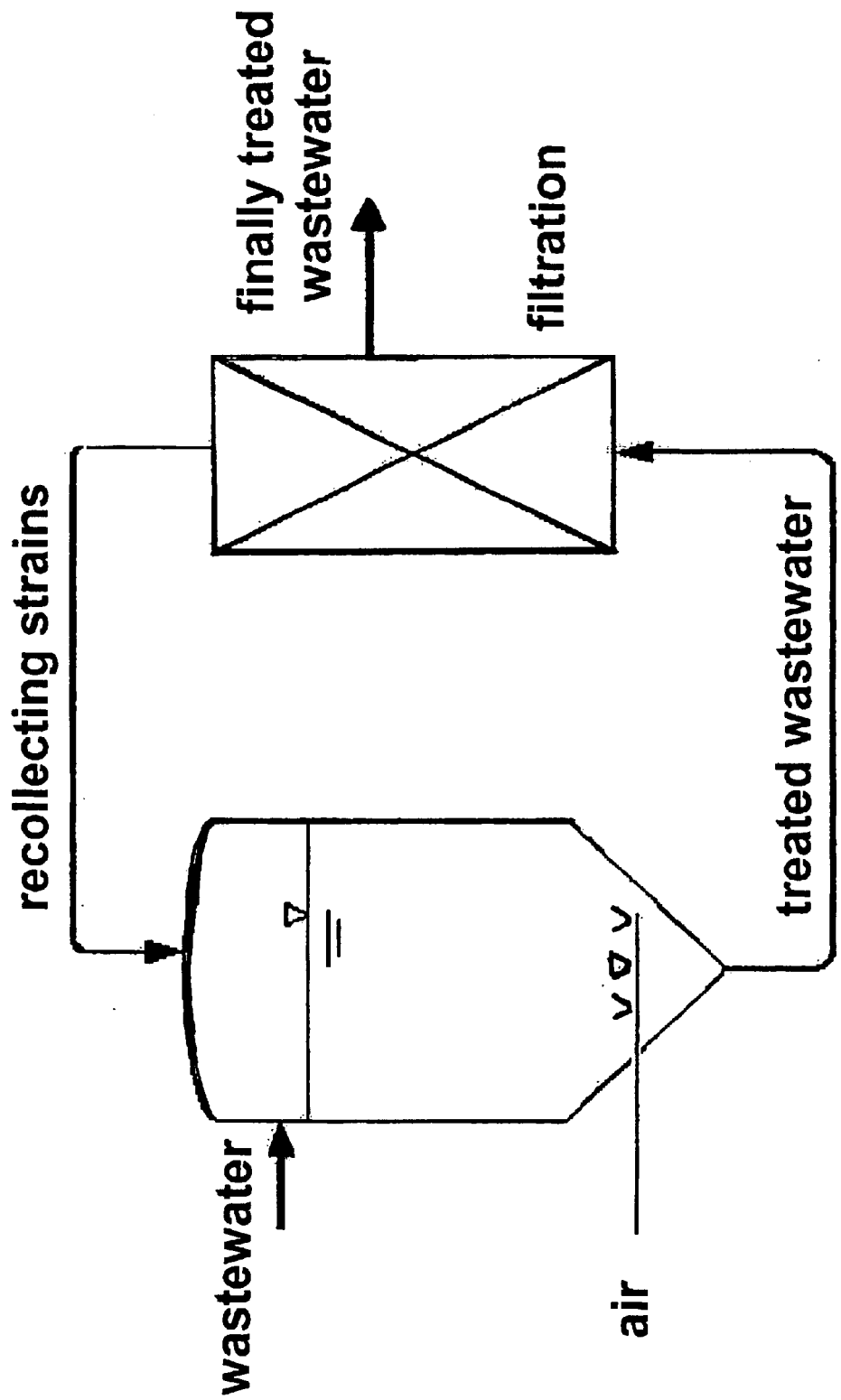
FIG. 9a shows the schematic diagram of the pilot system that represents the biological treatment process of TMAH by applying the microorganism strains of the present invention.
Figure 9B:
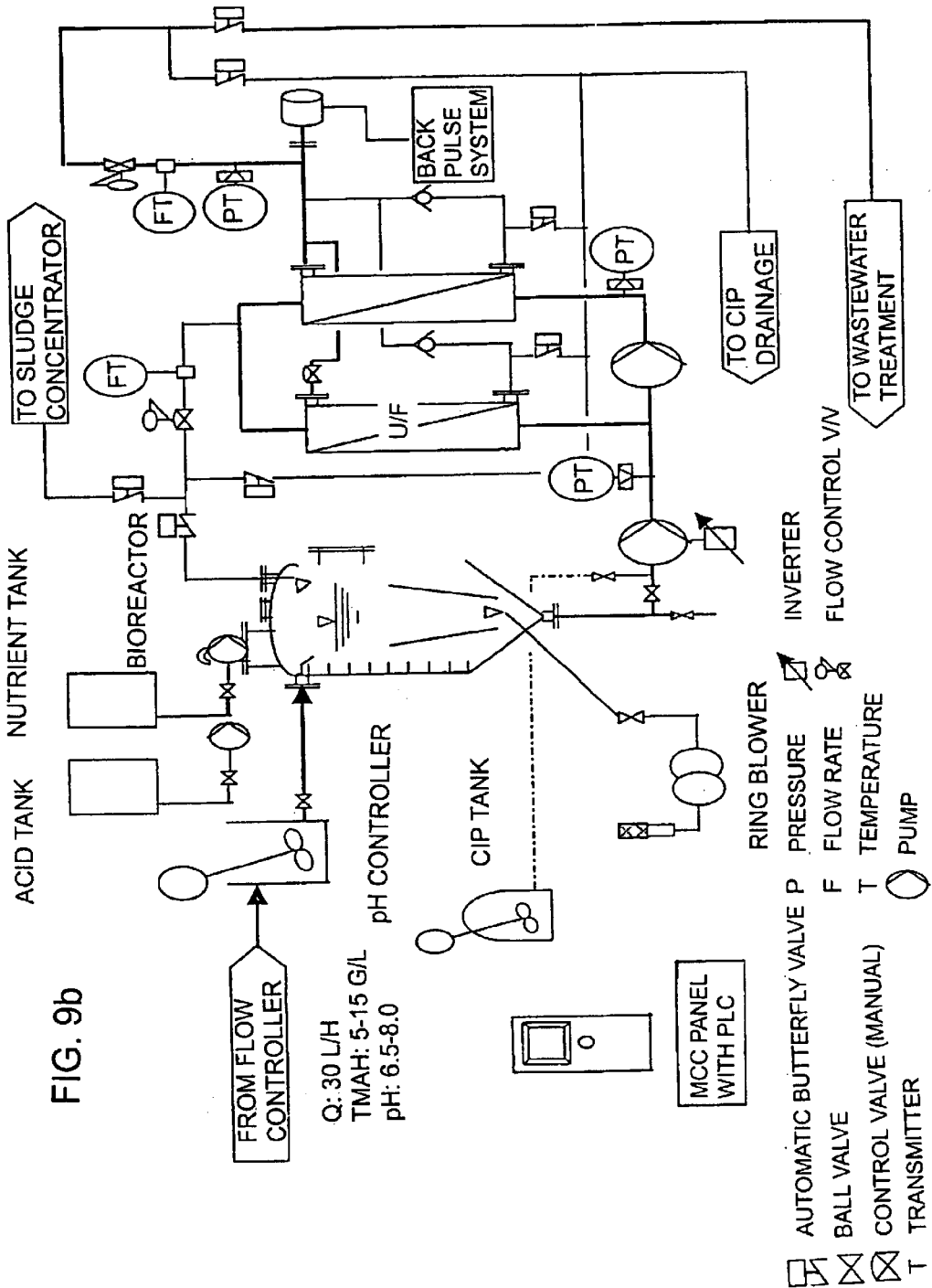
FIG. 9b shows the detailed diagram of pilot system that represents the biological treatment process of TMAH by applying the strains of the present invention; and, FIG. 10 shows the cell concentration as a function of the inlet TMAH concentration in the pilot system.

The cell recycle bioreactor having 200 L of volume capacity and 120 L of working capacity was used and a recycle filtration membrane (ceramic material, 0.1 μm of pore size) was adopted for preventing cells from outflowing (See FIG. 9a and FIG. 9b).

Generally, the TMAH concentration in discharging wastewater from the factory was comparatively low in 3~4 g/L. Hence, the concentrated TMAH solution was added into the wastewater directly for the convenience of the experiment. In detail, the TMAH concentration of the wastewater was adjusted to reach 5~15 g/L. By adding the concentrated TMAH solution to the outflowing wastewater in this Preferred Embodiment for the convenience. However, reverse osmosis system (RO) would be exploited in the practical application in order to concentrate TMAH of wastewater highly.

In addition, since the original wastewater contained excessive amount of TMAH relatively, the culture medium containing proper nitrogen sources (per 15 g TMAH: containing yeast extract 0.1 g, $(NH_4)_2SO_4$ 1 g, $MgSO_4.7H_2O$ 0.05 g) should be mixed to make Nutrient state required for the cell growth.

At that time, temperature (25~40° C.), air volume (1 vvm), pH (6.5~7.2) and so on was maintained properly and flow rate of wastewater and retention period were adjusted to 30 L/hour and 4 hour respectively during the treatment, which helped the cell growth environmentally.

Figure 10:
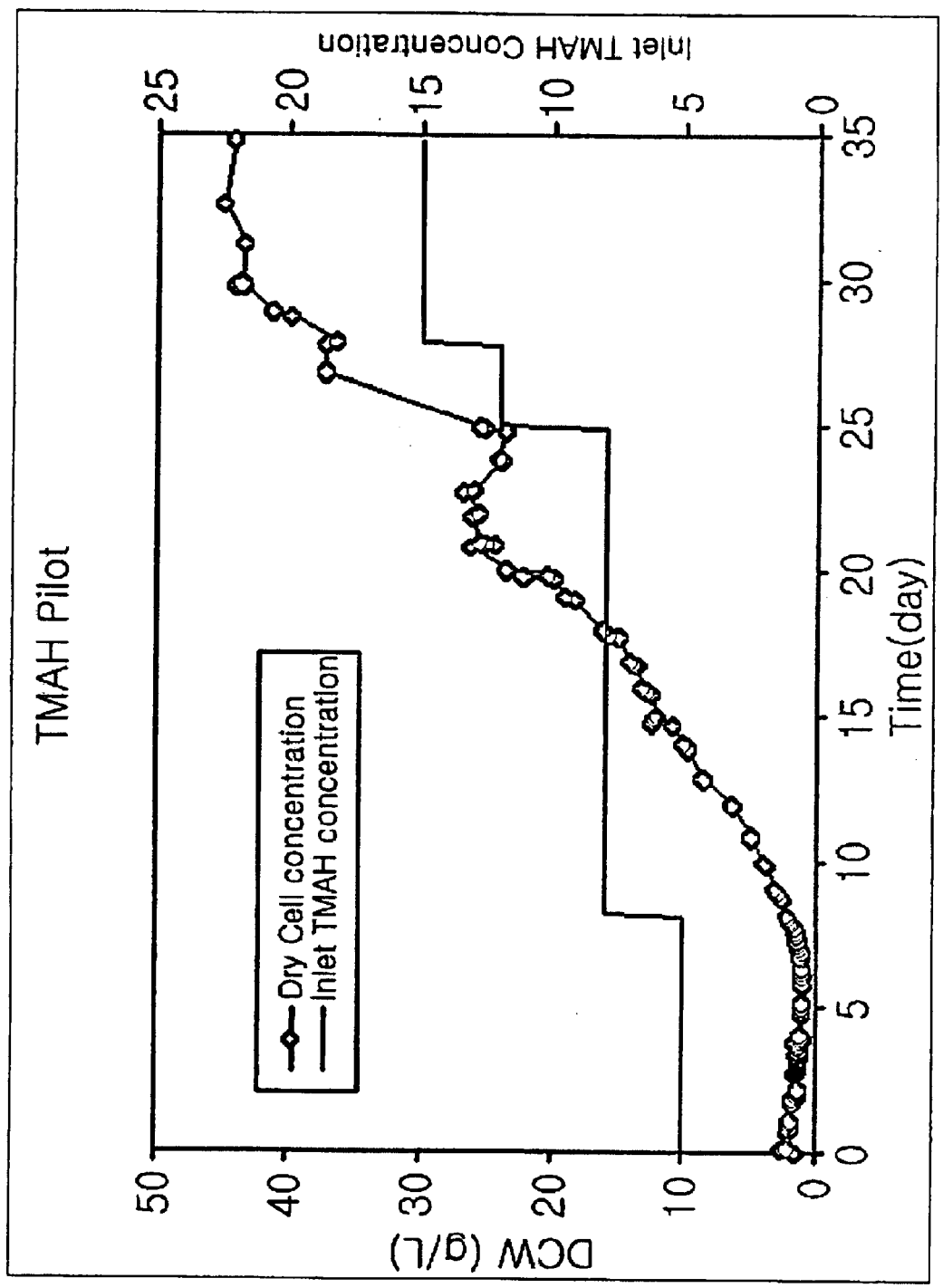

According to the reaction period and TMAH concentration of wastewater, the dried cell concentration was changed as demonstrated in FIG. 10 and the results were summarized in Table 9. As shown in Table 9, it was confirmed that the TMAH wastewater (5~15 g/L) having various concentrations was treated successfully (treatment efficiency 94~99%).

TABLE 9

Pilot experiment of biological TMAH treatment process by using the strains of the present invention.

| TMAH conc. of inflowing wastewater | BOD5 (ppm) of inflowing wastewater | BOD5 (ppm) of wastewater treated | Conc. of stable cell strains (g/L) | Treatment efficiency (%) |
|---|---|---|---|---|
| 5 | 10,000 | 50~70 | — | >99 |
| 8 | 16,000 | 400~600 | 24~25 | 96~97.5 |
| 12 | 24,000 | 1,000~400 | 36~37 | 94~95 |
| 15 | 30,000 | 400~600 | 43~44 | >98 |

Industrial Applicability

The present invention relates to novel strains decomposing tetramethyl ammonium hydroxide, which is often utilized in etching the surface of silicone chip while manufacturing semiconductors and is toxic and hard to be degraded. In addition, the present invention relates to a wastewater treatment method which comprises cultivating the above strains by using batch culture processes; applying the culture medium into TMAH containing wastewater; and performing continuous culture processes.

The novel strains of the present invention and the wastewater treatment process can decompose environmental contaminants TMAH over 95% existed in the wastewater of the semiconductor manufacturing facilities. Therefore, the wastewater treatment method of the present invention can be applied to industries as an environmental friendly wastewater treatment system efficiently.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the scope of the invention as set forth in the appended claims.

What is claimed is:

1. An isolated *Bacillus cereus* IBN-H4 strain (accession number: KCTC 0835 BP) which is insensitive to TMAH and uses TMAH as a carbon source for cell growth.

2. A biological wastewater treatment method for removing tetramethyl ammonium hydoxide, which utilizes an isolated *Bacillus cereus* IBN-H4 strain (acession number: KCTC 0835 BP) which is insensitive to TMAH and uses TMAH as a carbon source for cell growth.

3. The biological wastewater treatment method for removing tetramethyl ammonium hydoxide of wastewater according to claim 2, in which treatment is performed by batch culture.

4. The biological wastewater treatment method for removing tetramethyl ammonium hydoxide of wastewater according to claim 2, in which treatment is performed by continuous culture.

5. The biological wastewater treatment method for removing tetramethyl ammonium hydoxide of wastewater according to claim 4, in which the microorganism strain/strains is/are fixed onto a supporting carrier.

* * * * *

SEQUENCE LISTING

<160> NUMBER OF SEQ ID NOS: 2

<210> SEQ ID NO 1
<211> LENGTH: 585
<212> TYPE: DNA
<213> ORGANISM: Bacillus cereus IBN-H4

<400> SEQUENCE: 1

```
ggcggcgtgc ctaatacatg caagtcgagc gaatggatta agagcttgct cttatgaagt      60
tagcggcgga cgggtgagta acacgtgggt aacctgccca taagactggg ataactccgg     120
gaaaccgggg ctaataccgg ataacatttt gaacygcatg gttcgaaatt gaaaggcggc     180
ttcggctgtc acttatggat ggacccgcgt cgcattagct agttggtgag gtaacggctc     240
accaaggcaa cgatgcgtag ccgacctgag agggtgatcg gccacactgg gactgagaca     300
cggcccagac tcctacggga ggcagcagta gggaatcttc cgcaatggac gaaagtctga     360
```

-continued

```
cggagcaacg ccgcgtgagt gatgaaggct ttcgggtcgt aaaactctgt tgttagggaa      420
gaacaagtgc tagttgaata agctggcacc ttgacggtac ctaaccagaa agccacggct      480
aactacgtgc cagcagccgc ggtaatacgt aggtggcaag cgttatccgg aattattggg      540
cgtaaagcgc gcgcaggtgg tttcttaagt ctgatgtgaa agccc                      585

<210> SEQ ID NO 2
<211> LENGTH: 517
<212> TYPE: DNA
<213> ORGANISM: Acinetobacter sp. IBN-H7

<400> SEQUENCE: 2
gcggcaggct taacacatgc aagccgagcg ggcgaggttg cttcggtaac tgagctagcg      60
gcggacgggt gagtaatgct taggaatctg cctattagtg ggggacaaca ttccgaaagg     120
gatgctaata ccgcatacgt cctacgggag aaagcagggg ctctttatga ccttgcgcta     180
atagatgagc ctaagtcgga ttagctagtt ggtggggtaa aggcctacca aggcgacgat     240
ctgtagcggg tctgagagga tgatccgcca cactgggact gagacacggc ccagactcct     300
acgggaggca gcagtgggga atattggaca atgggggaa ccctgatcca gccatgccgc     360
gtgtgtgaag aaggcctttt ggttgtaaag cactttaagt ggggaggagg cttacctggt     420
taatacctgg gctaagtgga cgttacccac agaataagca ccggctaact ctgtgccagc     480
agccgcggta atacagaggg tgcgagcgtt aatcgga                               517
```